(12) United States Patent
Whittington et al.

(10) Patent No.: US 6,300,281 B1
(45) Date of Patent: Oct. 9, 2001

(54) OPTICALLY PURE(−) CLETHODIM, COMPOSITIONS AND METHODS FOR CONTROLLING PLANT GROWTH COMPRISING THE SAME

(75) Inventors: John Whittington, El Sobrante; Sandra Jacobsen, Walnut Creek; Allan Rose, Orinda, all of CA (US)

(73) Assignee: Valent U.S.A. Corporation, Walnut Creek, CA (US)

(*) Notice: Subject to any disclaimer, the term of this patent is extended or adjusted under 35 U.S.C. 154(b) by 0 days.

(21) Appl. No.: 09/609,770

(22) Filed: Jul. 3, 2000

(51) Int. Cl.$^7$ ............................ A01N 35/10; C07C 251/14
(52) U.S. Cl. ................................. 504/343; 564/256
(58) Field of Search .............................. 504/343; 564/256

(56) References Cited

U.S. PATENT DOCUMENTS

| | | | |
|---|---|---|---|
| 5,618,775 | 4/1997 | Misslitz et al. | 504/235 |
| 6,133,202 | * 10/2000 | Bratz et al. | 504/244 |

* cited by examiner

*Primary Examiner*—S. Mark Clardy
(74) *Attorney, Agent, or Firm*—Sughrue, Mion, Zinn, Macpeak & Seas, PLLC

(57) ABSTRACT

The invention relates to optically pure (−) clethodim, novel compositions of matter containing (−) clethodim substantially free from (+) clethodim, and methods of controlling vegetative growth employing such compositions.

22 Claims, No Drawings

OPTICALLY PURE(−) CLETHODIM, COMPOSITIONS AND METHODS FOR CONTROLLING PLANT GROWTH COMPRISING THE SAME

BACKGROUND OF THE INVENTION

1. Field of the Invention

The present invention is directed to optically pure (−) clethodim, novel compositions of matter containing (−) clethodim substantially free from (+) clethodim, and methods of controlling vegetative growth employing such compositions.

2. Description of the Related Art

Undesired vegetative growth in an agricultural setting can greatly impact the ultimate yield of crop plants. More commonly referred to as weeds, such growth can deplete the available water and nutrients available to desired plants, thereby inhibiting the growth of the desired plant and reducing the yield of useful plant materials. The use of herbicides to control plant growth has proven to be a successful means of countering the deleterious effects that weeds may have on crop growth.

Certain cyclohexanedione oximes are known in the art as having excellent herbicidal activity against a variety of post-emergent grasses in a variety of environments. Examples of cyclohexanedione oximes include clethodim, sethoxydim, cycloxydim, alloxydim, tralkoxydim, tepraloxydim, and clefoxydim. These compounds are characterized by a single ring structure that involves keto functions in the 1 and 3 positions with an oxime function in the 2 position. The significance of the structural similarity is revealed in the mode of action of these compounds, which involves chelation of metal ions associated with plant enzymes, otherwise responsible for promoting necessary biochemical reactions in the plant. This binding effect involves the oxime side chain and the enolic form of the 1,3-diketone to form a six-member ring incorporating the metal ion.

The 5 position substitutions of three of the cyclohexanedione oximes, clethodim, sethoxydim, and cycloxydim, contains a chiral carbon atom. As with many organic compounds, these three cyclohexanedione oximes exist in optically active forms, i.e., they have the ability to rotate the plane of plane-polarized light. In describing an optically active compound, the prefixes d and l or s and r are used to denote the absolute configuration of the molecule about its chiral center(s). The prefixes d and l, or (+) and (−) respectively, are employed to designate the sign of rotation of plane-polarized light by the compound, with (−) or l meaning that the compound is levorotatory. A compound prefixed with (+) or d is dextrorotatory. For a given chemical structure, these compounds, called stereoisomers, are identical except that they are mirror images of one another. A specific stereoisomer may also be referred to as an enantiomer, and a mixture of such enantiomers is often called an enantiomeric or racemic mixture. Enhanced activity of a single enantiomer, over that of a racemic mixture and the other opposite enantiomer, has not been taught or suggested based on studied modes of action of these compounds.

The active compound of the present invention is an optical isomer of the compound clethodim. Clethodim and related compounds are described in U.S. Pat. No. 4,440,566. The generic chemical structure of clethodim is shown below in formula I:

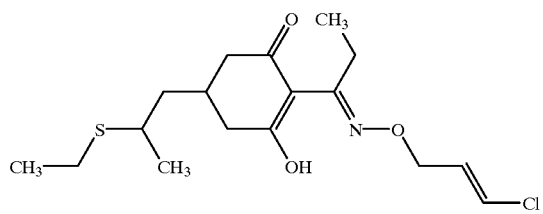

Clethodim (generic name), or Select® (trade name) (Valent U.S.A. Corp.), is a particularly important commercial herbicide within the class of cyclohexanedione oximes characterized by a 5 position substitution. It is generally systematically applied to crop plants, such as soybeans, so that the growth of grass weeds growing in the plot can be controlled. Select® is commercially produced as a composition comprising 26.4% clethodim by weight and 73.6% other ingredients, referred to as Select® 2EC (Valent U.S.A. Corp.), reflecting that it contains 2 pounds active ingredient (clethodim) per gallon. However, clethodim has only been used in the past as the 1:1 racemic mixture. That is, it is available only as a mixture of optical isomers. To applicants' knowledge, the individual isomers have not been isolated in pure or substantially pure form prior to the present invention.

While many effective herbicides, such as clethodim, have been developed, those skilled in the art will recognize that there is a need for herbicides with greater selectivity and improved effectiveness over current compounds. Use of such improved herbicides will result in decreased damage to non-target plants and reduced application rates, thereby reducing environmental effects and costs. This invention is directed to these, and other important ends.

SUMMARY OF THE INVENTION

It has now been discovered that the optically pure (−)-enantiomer of clethodim, which is (−)-2[(E)-1-[(E)-3-chloroallyloxyimino] propyl]-5-[2-(ethylthio)propyl]-3-hydroxycyclohex-2-enone, and will hereinafter be referred to as (−) clethodim, is surprisingly more effective in regulating the growth of grass plants than the corresponding racemic mixture or the optically pure (+)-enantiomer.

The present invention provides, in one aspect, optically pure (−) clethodim. This compound is the (−) or l optical isomer of the two isomers encompassed by formula (II):

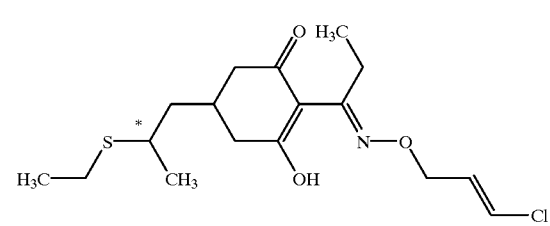

wherein the asterisk indicates the asymmetric or chiral carbon atom. In

Formula (II), it would be understood that the precise stereochemical configurations at the chiral center are not depicted.

In a further aspect, the present invention provides a herbicidal composition comprising a herbicidally-effective amount of (−) clethodim substantially free from (+) clethodim, as defined further herein.

The present invention also provides a method for controlling the growth of vegetation comprising, applying to the vegetation a herbicidal composition comprising a herbicidally-effective amount of (−) clethodim substantially free from (+) clethodim.

In an additional aspect, the method for controlling the growth of vegetation is used to control the growth of vegetation in a post-emergence growth stage.

DETAILED DESCRIPTION OF THE INVENTION

The presently available racemic mixture of clethodim (i.e., a 1:1 racemic mixture of the two stereoisomers) is a selective post-emergence herbicide for control of annual and perennial grasses in and around soybeans, cotton, sugar beets, onions (dry bulb only), garlic, shallots (dry bulb only), tomatoes, alfalfa, peanuts, dry beans, and non-bearing food crops.

It has now been unexpectedly discovered that (−) clethodim has increased potency compared to the racemic form or (+) clethodim when used in a herbicidal composition comprising a herbicidally-effective amount of (−) clethodim.

In one aspect, the present invention relates to optically pure (−) clethodim, which means the (−) or 1 isomer of clethodim synthesized by one of the methods described herein, or isolated in substantially optically pure form from the racemic mixture. "Substantially optically pure" form of the active compound, as used herein, means that the desired isomer is synthesized or isolated at 98–100%, preferably 100%, purity relative to the other optical isomer.

With respect to the term "substantially free from" as used herein means that the composition contains a greater proportion or percentage of the (−) or 1 enantiomer of clethodim, on a weight basis, in relation to the (+) or d enantiomer of clethodim, these percentages being based on the total amount of clethodim optical isomers present. In a preferred embodiment, the term "substantially free from" as used herein means that the composition contains at least 60% by weight of (−) or 1 clethodim enantiomer, and 40% by weight or less of the (+) or d enantiomer. In a more preferred embodiment, the term "substantially free from" means that the composition contains at least 75% by weight of (−) or 1 clethodim enantiomer, and 25% or less of the (+) or d enantiomer. In a still more preferred embodiment, the term "substantially free from" means that the composition contains at least 90% by weight of (−) or 1 clethodim enantiomer, and 10% or less of the (+) or d enantiomer. In an even more preferred embodiment, the term "substantially free from" means that the composition contains at least 99% by weight of (−) or 1 clethodim enantiomer, and 1% or less of the (+) or d enantiomer. In the most preferred embodiment, the term "substantially free from" means that the composition contains 100% by weight of (−) or 1 clethodim enantiomer, and none of the (+) or d enantiomer, again based on the total amount of clethodim.

In certain preferred embodiments of the present invention, the amount of (−) clethodim present in a desired composition is "herbicidally-effective." As used herein, the term "herbicide" means that a compound or composition negatively controls or modifies the growth of plants. Such controlling or modifying effects can include all deviations from natural development, such as killing, growth retardation, defoliation, desiccation, regulation, stunting, tillering, leaf burn, dwarfing, and the like. The term "herbicidally-effective amount" is meant to include any amount of such compound or composition which causes such negative modifying effect upon the growth of plants. Preferred application rates on a per acre basis are discussed below. The term "herbicidal composition" is meant to include compounds comprised of (−) clethodim substantially free from (+) clethodim which causes such negative modifying effect upon the growth of plants. The term "controlling" is meant to include all deviations from natural plant development, such as killing, growth retardation, defoliation, desiccation, regulation, stunting, tillering, leaf burn, dwarfing, and the like.

It will be recognized by those skilled in the art that certain herbicidal compositions are more effective in controlling the growth of plants at one stage or another. It will further be recognized by those skilled in the art that certain herbicidal compositions are more effective in controlling the growth of one plant species or another. Thus, it is within the purview of one skilled in the art to recognize or determine the stage and/or species for which application of a particular growth regulating composition of the present invention is most suitable.

It is generally desirable that a growth regulating composition used against undesired plant species destroy or prevent the growth of as much of an undesired plant species as feasible, such as, for example, by destroying at least about 80% of an established undesired plant. However, it will be recognized by those skilled in the art that suppression or destruction of plant growth at lower levels, particularly with some noxious and/or herbicide-resistant plants, can be commercially advantageous. Such suppression of plant growth is intended to fall within the scope of the present invention.

The methods and compositions of the present invention are useful in inhibiting or controlling the growth of plant species, including annual weeds. Preferably, the active compound of the present invention is differentially herbicidally active toward at least one desired plant species. By "differentially herbicidally active" is meant that the active compound may display less herbicidal activity toward a particular desired plant species as compared to their activity against one or more undesired plant species. In still more preferred embodiments, the methods and compositions of the present invention are substantially herbicidally inactive toward at least one desirable plant species. By "substantially inactive" is meant that the composition causes less than 20% damage to desired plant species. Such desirable plants are generally referred to as "crop plants." The term "crop plants," as used herein, includes any edible or non-edible, including decorative, plant species with commercial value, which is planted and cultivated for commercial use. Thus, crop plants include floral plants, trees, vegetable plants, and the like. The term "plants" is meant to include germinant seeds, emerging seedlings and established vegetation, including roots and above-ground portions.

Grass plants can be controlled using the compositions and methods of the present invention. Preferably, the grass plant to be controlled is in a post-emergent growth stage at the time of application of the herbicidal compositions of this invention. Examples of grass plant species against which the compositions and methods of the present invention are effective include, but are not limited to, the following:

| Annual grasses | |
|---|---|
| Barnyardgrass | *Echinochloa crus-galli* |
| Broadleaf Signalgrass | *Brachiaria platphylla* |
| Bromes | *Bromus species* |
| Crabgrasses | *Digitaria species* |
| Crowfootgrass | *Dactyloctenium aegyptium* |
| Fall Panicum | *Panicum dichotomiflorum* |
| Foxtails | *Setaria species* |
| Goosegrass | *Eleusine indica* |
| Itchgrass | *Rottboellia exaltata* |
| Junglerice | *Echinochloa colona* |
| Lovegrass (Stinkgrass) | *Eragrostis cilanensis* |
| Red Rice | *Oryza sativa* |
| Rygrasses | *Lolium species* |
| Seedling Johnsongrass | *Sorghum halepense* |
| Shattercane | *Sorghum bicolor* |
| Southwestern Cupgrass | *Eriochloa gracillis* |
| Sprangetops | *Leptochloa species* |
| Texas Panicum | *Panicum texanum* |
| Volunteer | |
| Barley | *Hordeum vulgare* |
| Oats | *Avena sativa* |
| Rye | *Secale cereale* |
| Wheat | *Triticum aestivum* |
| Corn | *Zea mays* |
| Grain Sorghum | *Sorghum bicolor* |
| Wild Oats | *Avena fatua* |
| Wild Proso Millet | *Panicum miliaceum* |
| Witchgrass | *Panicum capillare* |
| Woolly Cupgrass | *Eriochloa villosa* |
| Perennial grasses | |
| Bermudagrass | *Cynodon dactylon* |
| Fescue | *Festuca arundinacea* |
| Foxtail Barley | *Hordeum jubatum* |
| Orchardgrass | *Dactylis glomerata* |
| Quackgrass | *Agropyron repens* |
| Rhizome Johnsongrass | *Sorghum halepense* |
| Wirestem Muhly | *Muhlenbergia frondisa* |

Production of (−) Clethodim (−) Clethodim substantially free from (+) clethodim, as well as optically pure (−) clethodim, can be isolated from a racemic mixture of clethodim by preparative liquid chromatography using procedures well known to one of ordinary skill in the art. Racemic clethodim can be prepared as described in U.S. Pat. No. 4,440,566, incorporated by reference herein. Alternatively, (−) clethodim substantially free from (+) clethodim, as well as optically pure (−) clethodim, can be produced by the following method.

a) Preparation of 3-Ethylthiobutanal (−) Clethodim may be prepared by first reacting ethanethiol and crotonaldehyde (ca. equal molar amounts), in the presence of catalytic triethylamine (ca. 10 mole %), to yield 3-ethylthiobutanal (ETB) (formula III; the asterisk denotes the chiral center). The reaction is known to proceed spontaneously.

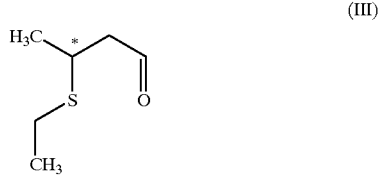

(III)

A refinement of crude ETB is performed by applying a vacuum to the crude ETB to remove contaminating water and ethanethiol. The resulting residue is taken up in diethyl ether and dried over sodium sulfate. The resulting filtrate is concentrated on a rotary evaporator and then maintained under high vacuum to yield an amber oil. Product identity in each step may be verified by NMR, and purity may be determined by gas chromatography (GC) area %.

b) Preparation of Racemic Aldol

A mixture of methyl acetoacetate and water is placed in a round bottom flask and blanketed with nitrogen. Sodium hydroxide is added (ca. equal molar amount), with external cooling to maintain the exotherm to less than 30° C. The resulting slurry is stirred at ambient temperature overnight. The pH is adjusted to approximately neutral by addition of concentrated hydrochloric acid. To this mixture is added methanol and triethylamine (ca. 10 mole %), followed by addition of 3-ethylthiobutanal (ca. equal molar amount). The resulting exotherm (ca. 5–10° C) is allowed to proceed unchecked. Stirring is continued under heat for several hours, and then overnight at ambient temperature. Concentrated hydrochloric acid is added to obtain an acidic pH. The aqueous layer is separated, and extracted with diethyl ether. The diethyl ether extract is then combined with the organic layer. The combined organic layer is concentrated on a rotary evaporator, and then mixed with benzene. Residual water is removed as an azeotrope, and the remaining benzene is stripped. The residue is maintained under high vacuum to remove residual lights. An amber oil (the racemic aldol intermediate of formula IV) is obtained. Note that a second, transitory, chiral center is present in the structure specified in formula IV (denoted by •).

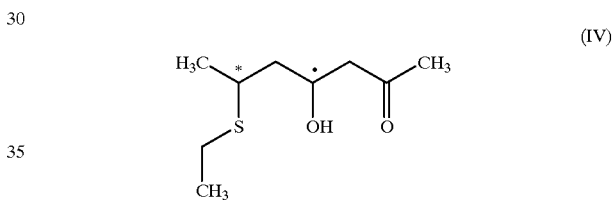

(IV)

c) Determination of Specific Rotations and Preparation of Chiral Aldol

A small portion of the racemic aldol intermediate is separated into its four enantiomers on a preparative HPLC column. The samples are treated with phosphoric acid, as described in the next section, to eliminate the second chiral center and allow unambiguous determination of specific rotations. The remainder of the racemic aldol is then processed through, and the appropriate peaks identified, allowing collection of the target (−)-enantiomer in the desired amount relative to the (+)-enantiomer. (+) Clethodim can also be made using this method, however, at this step the (+)-enantiomer would be collected and processed through the remainder of the steps, if desired.

The refinement of these separations determines the degree of optical purity. Optically pure enantiomers of 99–100% purity can be obtained through efficient separation. The optical purity of the clethodim isomer derived from these separated intermediates is the same as the intermediates themselves since no change in optical orientation is created by the additional reactions required to produce clethodim. Thus, optically pure enantiomers of 100% purity can be obtained under the described conditions. However, in practice, less than 100% optical purity is adequate to practice the principles of the invention, within the ranges defined above.

d) Preparation of Unsaturated Ketone

The (−) chiral aldol intermediate is mixed with phosphoric acid (ca. equal molar amounts) and benzene. The mixture is stirred under heat and then allowed to cool to ambient temperature. A sample of the organic layer is analyzed by GC to verify completion of the reaction. The aqueous layer is separated and discarded. The organic layer is washed with water and sodium bicarbonate, then dried over sodium sulfate, filtered, and stripped, producing RE-35747 (formula V). The dehydration introduces a double bond and eliminates the second chiral center (see formula V).

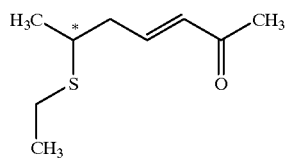

(V)

e) Dione Synthesis

Sodium methoxide (25% solution in methanol) is added to a mixture of the RE-35747 intermediate and dimethyl malonate (ca. equal molar amounts), with cooling as required to sustain ambient temperature. The mixture is then stirred overnight at ambient temperature. Reaction completion is verified by thin layer chromatography. With external cooling, ice water is added, and then concentrated hydrochloric acid to obtain an acidic pH. The aqueous layer is separated and discarded. The organic layer is washed with brine, dried over sodium sulfate, filtered and concentrated on a rotary evaporator. The reaction product is RE-45 104 (formula VI).

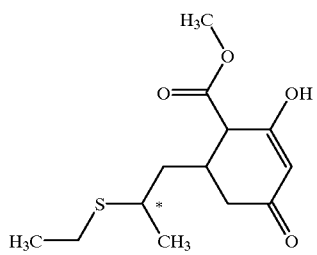

(VI)

f) Trione Synthesis

The RE-45104 intermediate is combined with propionic anhydride (ca. equal molar amounts), toluene and 4-(dimethylamino)pyridine (ca. 10 mole %), and stirred under heat. Reaction completion, yielding the adduct of formula VII (RE-47073), is verified by thin layer chromatography.

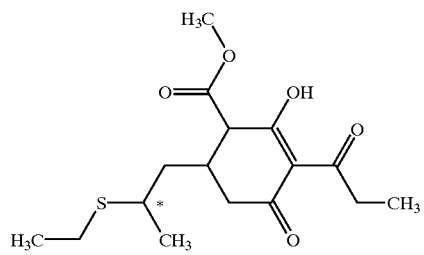

(VII)

The carbomethoxy group, as depicted in formula VII, is removed by cooling the adduct to ambient temperature, and then adding sodium hydroxide (25% solution; ca. 4 molar equivalents). The exotherm (ca. 10–20° C.) is permitted to proceed unchecked. The mixture is then stirred under heat. Thereafter, it is cooled to ambient temperature, separated and the organic layer is discarded. To the aqueous layer is added hexanes and then heat. Concentrated hydrochloric acid is added to reduce the mixture to an acidic pH and facilitate decarboxylation. This mixture is then stirred under heat to assure completion of decarboxylation. It is then cooled to ambient temperature, separated, and the aqueous layer is discarded. The organic layer is dried over sodium sulfate, filtered and stripped on a rotary evaporator to yield an amber oil, RE-45550 (formula VIII).

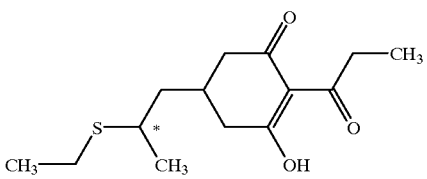

(VIII)

g) Clethodim Synthesis

The RE-45550 trione intermediate and 3-chloropropenyl-oxyamino hydrochloride (ca. equal molar amounts) are reacted in a mixed hexanes-water system that has been adjusted to pH 5.5–6.0, with sodium hydroxide, and buffered by addition of acetic acid. The exotherm (ca. 5–10° C.) is permitted to proceed unchecked. The reaction mixture is then stirred overnight at ambient temperature. Reaction completion is verified by HPLC analysis. The aqueous layer is separated and discarded. To the organic layer is added water and then sodium hydroxide to pH 12–14. The organic layer is separated and discarded. To the aqueous layer is added hexanes and then concentrated hydrochloric acid to obtain an acidic pH. The aqueous layer is separated and discarded. The organic layer is washed with water and then dried over sodium sulfate and stripped to yield an amber oil.

Analysis of the resulting (−)-enantiomer includes verification of generic identity by NMR analysis and determination of chiral identity by specific rotation and separation under chiral HPLC conditions to determine enantiomeric excesses. Equal and opposite specific rotations $[\alpha]_D^{24}=28°$ (C=ca. $6\times10^{-3}$ M in methanol) are determined on a polarimeter.

Production of Herbicidally-effective Formulations Comprising (−) Clethodim Substantially Free from (+) Clethodim The herbicidal composition of the present invention is comprised of (−) clethodim substantially free from (+) clethodim, as defined above. The amount of (−) clethodim substantially free from (+) clethodim contained in herbicidal compositions of the present invention can be readily determined for particular crop plants and particular weed families by persons skilled in the art, depending on many factors, including the species of plant and its growth stage, row and plant spacing, environmental conditions, weather, etc. In general, however, it has been determined that suitable ranges of (−) clethodim substantially free from (+) clethodim in herbicidal compositions of the present invention are from about 0.010 to 0.25 pounds active ingredient per acre (lbai./A), preferably from about 0.022 to 0.12 lbai./A, more preferably from about 0.045 to 0.094 lbai./A, with more preferred ranges depending upon application, as discussed herein below.

While the herbicidal composition comprising a herbicidally-effective amount of (−) clethodim substantially free from (+) clethodim of the present invention may be comprised solely of (−) clethodim, it is preferred that the formulation also includes one or more adjuvants. Useful adjuvants include, without limitation, crop oil concentrates, surfactants, fertilizers, emulsifiers, dispersing agents, foaming activators, foam suppressants, and correctives. Adjuvants generally facilitate the entry of (−) clethodim through plant cell walls. The usefulness of a particular adjuvant depends on, among other factors, the species of the plant being treated with the formulation of the invention, the plant's growth stage and the related environmental conditions.

In a preferred embodiment, the one or more adjuvants in the herbicidal composition is a crop oil concentrate. Crop oil concentrates are generally comprised of from 65–96% by weight of a hydrocarbon oil or solvent with the balance being a surfactant. The hydrocarbons may be petroleum or vegetable based. Exemplary crop oil concentrates found to be useful in the formulations of this invention include Agridex (HELENA Chemical Co.). Preferably between about 0.05 and 5% v/v of a crop oil concentrate is included in the herbicidally-active formulation of the present invention. More preferably, the crop oil concentrate is 0.5 to 1.5% v/v, most preferably the crop oil concentrate is 1% v/v.

In a preferred embodiment, the herbicidally-effective composition of the present invention is produced by mixing (−) clethodim substantially free from (+) clethodim into a spray mixture by adding, on a acre equivalent basis, half of the required water, the clethodim dose, and the adjuvant, and then bringing the mixture to 100% by adding the remaining amount of water.

Although one of ordinary skill in the art will understand that various volumes of the herbicidally-effective formulation may be prepared, depending on the size of the area to be treated, 20 gallons is a useful volume. As such, this embodiment of the herbicidally-effective composition can be produced by adding 10 gallons of water to a spray tank. Next, between about 0.010 to 0.25 pounds (−) clethodim substantially free from (+) clethodim, preferably between about 0.022 to 0.12 pounds, more preferably between about 0.045 to 0.094 pounds, are mixed into the tank. Then, between about 1 and 100 ounces of a crop oil concentrate, preferably between about 10 to 50 ounces, most preferably about 25 ounces, is mixed into the solution. Finally, water is added to bring the final volume to 20 gallons.

One of ordinary skill in the art will understand that (−) clethodim substantially free from (+) clethodim can be used as the only active ingredient in a herbicidal composition, or that it can be used in combination with one or more other active chemicals. As used in the present invention, the term "other active chemicals" refers to other chemicals that possess biological activity, such as plant disease control agents including insecticides, fungicides, bacteriocides, nematicides, and other herbicides.

In a preferred embodiment, the one or more other active chemicals in the herbicidally-effective composition is a secondary herbicide. Non-limiting examples of acceptable secondary herbicides include 2,4-DB, Assure®/Assure II, Basagran®, Classicg, Cobra®, Firstrate®, Fusilade® DX, Option®, Passport®, Pinnacleg, Pursuit®, Pursuit Plus®, Reliance™ STS®, Roundup Ultra®, Scepter®, Stellar®, and Synchrony™ STS®. A herbicidally-effective composition containing a secondary herbicide is produced by mixing the secondary herbicide into water, followed (−) clethodim substantially free from (+) clethodim, and a crop oil concentrate (if any). For a 15 gallon herbicidally-effective formulation, the mixture can be produced by mixing between about 0.005 and 10 pounds of the secondary herbicide active ingredient into 15 gallons of water, more preferably between about 0.5 and 5 pounds, most preferably about 1 pound. The remaining ingredients are then mixed into the formulation as directed above.

One of ordinary skill in the art will also understand that biologically inert carriers may be included in all embodiments of the herbicidal compositions of the present invention. Other active chemicals or inert ingredients may be used to provide a more satisfactory formulation, provided the chemicals or ingredients do not detract from the effect of the essential components of the invention.

Application of Herbicidally-effective Formulations Comprising (−) Clethodim Substantially Free from (+) Clethodim One of ordinary skill in the art will understand that the methods of the invention may be practiced by applying a formulation comprising (−) clethodim substantially free from (+) clethodim alone, although it is preferred that at least one adjuvant is present in the formulation. The methods of the invention may be practiced by applying a herbicidally-effective composition comprising (−) clethodim substantially free from (+) clethodim, one or more adjuvants, with or without other active chemicals, and with or without other inert ingredients. Furthermore, it will be understood that the (−) clethodim substantially free from (+) clethodim, one or more adjuvants, other active chemicals, and other inert ingredients may be applied concurrently or sequentially (in any desired sequence) so long as each component will perform as intended in accordance with the invention. If applied sequentially, the individual components may be applied over a short or long time frame.

The herbicidally-effective formulation of this invention may be applied to the surface of the plant in a single application until the leaves of the plant are partially wetted, fully wetted or until runoff. The formulation may be applied at any time of day or night with good resulting activity, but preferentially should not be applied within 30 minutes of a predicted rainfall. The application can be repeated as often as considered useful. In a preferred embodiment, the formulation is applied by spraying the formulation onto the plants. Non-limiting examples of means for spraying the formulation onto plants include a tractor boom sprayer, a hand held aerosol sprayer, air blast sprayer, and helicopter or fixed-wing aircraft boom sprayer. Preferably, the sprayer is calibrated to deliver the formulation at between about 1 and 100 gallons per acre, more preferably between about 3 and 40 gallons per acre, most preferably about 20 gallons per acre.

It will be apparent to one of ordinary skill in the art that the "herbicidally-effective amount" of (−) clethodim substantially free from (+) clethodim required to control plant growth will be largely variable, depending on many factors, including the species of plant and its growth stage, row and plant spacing, environmental conditions, weather, etc. In general however, it has been determined that a herbicidally-effective composition comprised of (−) clethodim substantially free from (+) clethodim, applied in amounts generally between about 0.01 and 0.25 pounds active ingredient per acre, adequately controls the growth of plants to which it is applied. More preferably, between about 0.022 and 0.12 pounds active ingredient per acre is used to control plant growth. Most preferably, about from 0.045 to 0.094 pounds active ingredient per acre is used to control plant growth.

In a preferred embodiment, the herbicidally-effective composition applied to plants is comprised of (−) clethodim substantially free from (+) clethodim and a crop oil concentrate. Preferably, the (−) clethodim substantially free from (+) clethodim of the composition is applied within the range discussed above. Preferably, the crop oil concentrate of the composition is applied at a rate of between about 1 and 100 fluid ounces per acre, more preferably between about 10 and 50 fluid ounces per acre, most preferably about 25 fluid ounces per acre.

Again, it is anticipated that within these general guidelines, one of ordinary skill in the art would be readily able to select an appropriate formulation and application volume per acre, to achieve the objects and advantages of the present invention.

EXAMPLES

The following examples are merely illustrative of the preferred aspects of the invention and are not to be construed as limiting in any way. In the Examples as well as other parts of this application, all parts, percents, ratios and the like are by weight unless otherwise indicated.

Example 1

Preparation of (−) Clethodim and (+) Clethodim a) Preparation of 3-Ethylthiobutanal Approximately 250 grams of crude 3-ethylthiobutanal oil (formula II) (Eastman Chemical Co.) were maintained under high vacuum for several hours to remove contaminating water and ethanethiol. The resulting residue was taken up in 250 ml diethyl ether and dried over sodium sulfate. The resulting filtrate was concentrated on a rotary evaporator and then maintained under high vacuum for approximately four hours to yield approximately 220 g of amber oil. Product identity was verified by NMR, and purity (~98%) was determined by gas chromatography (GC) area %.

b) Preparation of Racemic Aldol

A mixture of methyl acetoacetate (58 g; 0.5 mole; Aldrich Chemical Co.) and water was placed in a 250 ml round bottom flask and blanketed with nitrogen. Sodium hydroxide (42.8 g of a 50% solution; 0.535 mole) was added dropwise over 15 minutes, with external cooling to maintain the exotherm to less than 30° C. The resulting slurry was stirred at ambient temperature overnight. With overnight stirring, the mixture changed from a slurry to a clear solution. The pH was adjusted to 8.5 by addition of concentrated hydrochloric acid (volume as required). To this mixture was added 75 ml methanol and triethylamine (1 g; 10 mmole; Aldrich Chemical Co.), followed by addition of 3-ethylthiobutanal (47.6 g; 0.36 mole) dropwise over 10 min. The resulting exotherm was allowed to proceed unchecked (to ~27° C). Stirring was continued for 5 hours at 45° C., and then overnight at ambient temperature. Concentrated hydrochloric acid was added at ambient temperature dropwise (volume as required), to obtain a pH of 3.0. Vigorous carbon dioxide evolution occurred around pH 7.0. The bottom (aqueous) layer was separated, and extracted with diethyl ether. The diethyl ether extract was then combined with the top (organic) layer. The combined organic layer was concentrated on a rotary evaporator, and then mixed with benzene. Residual water was removed as an azeotrope, and the remaining benzene was stripped. The residue was maintained under high vacuum to remove residual lights. 60 grams of amber oil (the racemic aldol intermediate of formula III) was obtained (~88%). The target structure was confirmed by NMR.

c) Determination of Specific Rotations and Preparation of Chiral Aldol

A small portion of the racemic aldol intermediate was separated into its four enantiomers on a preparative HPLC column (CHARACEL® OJ™, 10 cm×50 cm). The samples were treated with phosphoric acid, as described in the next section, to eliminate the second chiral center and allow unambiguous determination of specific rotations. The remainder of the racemic aldol was then processed through, and the appropriate peaks identified, allowing collection of the target (−) and (+) enantiomers. Theoretically, optically pure enantiomers of 100% purity can be obtained under the described conditions. In this example, however, enantiomers of 90–95% purity were obtained.

d) Preparation of Unsaturated Ketone

The remainder of the steps was performed with both the (−) and (+) enantiomers, though in separate vessels. Each selected chiral aldol intermediate (4.75 g; 25 mmole) was mixed with phosphoric acid (2.88 g of 85% solution; 25 mmole) and 25 ml of benzene. The mixture was stirred at 65° C. for several hours and then allowed to cool to ambient temperature. A sample of the organic layer was analyzed by GC to verify completion of the reaction. The bottom (aqueous) layer was separated and discarded. The organic layer was washed with water and 5% sodium bicarbonate, then dried over sodium sulfate, filtered and stripped. The reaction product (RE-35747 of formula IV) was used in the next reaction with assumed 100% yield.

e) Dione Synthesis

Sodium methoxide (6.5 g of 25% solution in methanol; 30 mmole) was added dropwise to a mixture of the RE-35747 intermediate (in benzene as specified) and dimethyl malonate (3.3 g; 25 mmole), over several minutes with cooling required to sustain ambient temperature. The mixture was then stirred overnight at ambient temperature. Reaction completion was verified by thin layer chromatography. With external cooling, 25 ml ice water was added, and then concentrated hydrochloric acid (volume as required) to reduce the pH to 3.0. The bottom (aqueous) layer was separated and discarded. The organic layer was washed with 10 ml brine, dried over sodium sulfate, filtered and concentrated on a rotary evaporator. The reaction product (RE-45104 of formula V) was used in the next reaction with an assumed yield of 100%.

f) Trione Synthesis

The RE-45104 intermediate was combined with 10 ml toluene, propionic anhydride (3.25 g; 25 mmole) and 4-(dimethylamino) pyridine (0.31 g; 2.5 mmole), and stirred for five hours at 90° C. Reaction completion, yielding the adduct of formula VI (RE-47073), was verified by thin layer chromatography.

The adduct was cooled to ambient temperature, and then sodium hydroxide (16 g of 25% solution; 100 mmole) was added. The exotherm was permitted to proceed unchecked (to 35° C). The mixture was then stirred for several hours at 40° C. Thereafter, it was cooled to ambient temperature, separated and the top (organic) layer was discarded. To the bottom (aqueous) layer was added 25 ml hexanes which was then heated to 55° C. Concentrated hydrochloric acid was added (volume as required) dropwise over 10 min. to lower the pH to 3.0. Vigorous carbon dioxide evolution occurred around pH 6.0. This mixture was stirred for several hours at 55° C. to assure completion of decarboxylation. It was then cooled to ambient temperature, separated, and the bottom (aqueous) layer was discarded. The top (organic) layer was dried over sodium sulfate, filtered and stripped on a rotary evaporator to yield 3.6 g amber oil (13.4 mmole; ~54% yield for three steps). The target structure (RE-45550 of formula VII) was confirmed by NMR.

g) Clethodim Synthesis

The RE-45550 trione intermediate (3.6 g; 13.4 mmole) was combined with 12 ml hexanes, 6 ml of water and acetic acid (0.5 g; 8 mmole). To this mixture was added the 3-chloropropenyl-oxyamino hydrochloride (2.12 g; 14.7 mmole; Chevron Chemical Co.), followed by addition of sodium hydroxide (volume as required) to reduce the pH to 5.8. The exotherm was permitted to proceed unchecked (to 27° C.). The reaction mixture was then stirred overnight at ambient temperature. Reaction completion was verified by HPLC analysis. The bottom (aqueous) layer was separated and discarded. To the top (organic) layer was added 20 ml water and then sodium hydroxide (volume as required) to pH 13. The top (organic) layer was separated and discarded. To the bottom (aqueous) layer was added 20 ml hexanes and then concentrated hydrochloric acid (volume as required) to pH 4.0. The bottom (aqueous) layer was separated and discarded. The top (organic) layer was washed with 10 ml water and then dried over sodium sulfate and stripped to yield 3.9 g (10.9 mmole; 81%) amber product oil.

Analysis of each enantiomer included verification of generic identities by NMR analysis and determination of chiral identities by specific rotation and separation under chiral HPLC conditions to determine enantiomeric excesses. Equal and opposite specific rotations $[\alpha]_D^{24}=28°$ (C=ca. $6\times10^{-3}$ M in methanol) were determined on a Rudolph AutoFill II polarimeter. Absolute configurations were not determined. Enantiomeric excesses (>90% for each test sample) were determined using a Regis, Pickle Covalent (RJR) Whelk-01 analytical HPLC column (25 cm×4.6 mm, 5μ).

Example 2

Herbicidal Screening

Test compounds ((−) clethodim obtained in Example 1 (90–95% optical purity), (+) clethodim obtained in Example 1 (90–95% optical purity), and racemic clethodim (Select® 2EC)) were applied to eight different plant species (Table I) in a spray mixture, using several different concentrations, to evaluate the growth regulating abilities of each compound. The clethodim treatment rates ranged between 0.03 to 0.12 pounds of active ingredient per acre. Each spray mixture contained the crop oil concentrate Agridex at the concentration of 32 fluid ounces per acre. The total spray volume was 20 gallons per acre. Each spray mixture was prepared by adding, on an acre equivalent basis, half of the required water, the clethodim dose, and the adjuvant. The mixture was then brought to 100% by adding the remaining amount of water. Each spray mixture was then sprayed on to the test plots using a tractor sprayer calibrated to deliver 20 gallons per acre.

The growth stage and height of each plant species included in the assay, at the time the test compounds were applied to the test plots, are listed in Table I. Weed control observations were made 7, 14 and 28 days after application of the test compounds. All treatments were replicated three times.

The results shown in Table II demonstrate that (−) clethodim substantially free from (+) clethodim provides a surprisingly greater degree of growth control than either the racemic form or (+) clethodim substantially free from (−) clethodim against each of the species tested. Results are expressed as a relative percentage of dead plants in a treated plot versus an untreated plot.

When using (−) clethodim substantially free from (+) clethodim, the herbicidal rates may range from 0.03 to 0.09 pounds active ingredient per acre, compared with the equivalent rate range of 0.06 to 0.12 for the racemic mixture, for the same effect. Thus, with the enantiomer of the invention, the rates can be lowered and the maximum lethal dosage is reached at a lower level.

TABLE I

| Plant | | | Growth stage at | Height at |
| --- | --- | --- | --- | --- |
| Common name | Botanical name | Bayer code | application | application (in.) |
| Corn, volunteer | Zea mays | SUMACS | 5 leaf | 22–30 |
| Shattercane | Sorghum album | SERVO | 2 tiller | 12–20 |
| Johnsongrass, seedling | Sorghum halepense | SHROUD | 1 tiller | 9–13 |
| Barnyardgrass | Echinochloa crus-galli | ECHCG | 2 tiller | 3–7 |
| Giant foxtail | Setaria faberi | SETFA | 2 tiller | 6–11 |
| Soybean (Roundup Ready) | Glycine max | GLYMB2 | 4 leaf | 6–8 |
| Sorghum, grain | Sorghum bicolor | SORGH | 6 leaf | 23–27 |
| Corn, volunteer (Poast Protected) | Zea mays | ZEAMX5 | 5 leaf | 21–31 |

TABLE II

PERCENT CONTROL

| Day | Rate | ZEAMX | | | SORVU | | | SORHA1 | | | ECHCG | | | SETFA | | | GLYMB2 | | | SORGH | | | ZEAMX5 | | |
| --- | --- | --- | --- | --- | --- | --- | --- | --- | --- | --- | --- | --- | --- | --- | --- | --- | --- | --- | --- | --- | --- | --- | --- | --- | --- |
| | | − | + | −/+ | − | + | −/+ | − | + | −/+ | − | + | −/+ | − | + | −/+ | − | + | −/+ | − | + | −/+ | − | + | −/+ |
| 7 | 0.030 | 40 | 18 | 33 | 62 | 43 | 63 | 76 | 57 | 66 | 77 | 61 | 67 | 70 | 58 | 63 | 0 | 0 | 0 | 35 | 25 | 36 | 14 | 11 | 17 |
| | 0.060 | 53 | 33 | 55 | 71 | 56 | 63 | 84 | 72 | 75 | 83 | 71 | 80 | 74 | 60 | 64 | 0 | 0 | 0 | 42 | 35 | 40 | 37 | 8 | 29 |

TABLE II-continued

| | | ZEAMX | | | SORVU | | | SORHA1 | | | ECHCG | | | SETFA | | | GLYMB2 | | | SORGH | | | ZEAMX5 | | |
|---|---|---|---|---|---|---|---|---|---|---|---|---|---|---|---|---|---|---|---|---|---|---|---|---|---|
| Day | Rate | − | + | −/+ | − | + | −/+ | − | + | −/+ | − | + | −/+ | − | + | −/+ | − | + | −/+ | − | + | −/+ | − | + | −/+ |
| | 0.090 | 53 | 37 | 52 | 75 | 69 | 68 | 81 | 74 | 84 | 91 | 73 | 80 | 75 | 65 | 73 | 0 | 0 | 0 | 38 | 37 | 43 | 38 | 25 | 23 |
| | 0.120 | 45 | 33 | 47 | 79 | 69 | 75 | 86 | 78 | 88 | 94 | 78 | 93 | 74 | 71 | 72 | 0 | 0 | 0 | 40 | 27 | 42 | 33 | 15 | 35 |
| 14 | 0.030 | 62 | 25 | 42 | 82 | 60 | 78 | 96 | 62 | 87 | 97 | 73 | 94 | 88 | 73 | 85 | 0 | 0 | 0 | 50 | 27 | 45 | 18 | 10 | 17 |
| | 0.060 | 75 | 42 | 60 | 95 | 78 | 89 | 98 | 89 | 97 | 99 | 95 | 98 | 96 | 83 | 94 | 0 | 0 | 0 | 72 | 40 | 60 | 42 | 12 | 28 |
| | 0.090 | 81 | 57 | 75 | 98 | 83 | 93 | 98 | 95 | 98 | 99 | 95 | 98 | 97 | 89 | 95 | 0 | 0 | 0 | 75 | 45 | 67 | 47 | 30 | 33 |
| | 0.120 | 82 | 50 | 79 | 98 | 83 | 96 | 98 | 97 | 98 | 100 | 97 | 100 | 97 | 94 | 97 | nd | 0 | 0 | 81 | 40 | 73 | 53 | 27 | 55 |
| 28 | 0.030 | 68 | 28 | nd | 74 | 43 | nd | 94 | 62 | nd | 98 | 75 | nd | 96 | 78 | nd | 0 | 0 | nd | 57 | 33 | nd | 10 | 8 | nd |
| | 0.060 | 96 | 43 | nd | 99 | 62 | nd | 99 | 80 | nd | 99 | 99 | nd | 98 | 95 | nd | 0 | 0 | nd | 91 | 47 | nd | 40 | 17 | nd |
| | 0.090 | 99 | 65 | nd | 98 | 77 | nd | 99 | 91 | nd | 100 | 99 | nd | 99 | 98 | nd | 0 | 0 | nd | 96 | 52 | nd | 45 | 28 | nd |
| | 0.120 | nd | nd | nd | nd | nd | nd | nd | nd | nd | nd | nd | nd | nd | nd | nd | nd | nd | nd | nd | nd | nd | nd | nd | nd |

Data are the means of three replicates.
− clethodim is represented by "−."
+ clethodim is represented by "+."
Racemic clethodim is represented by "−/+."
nd = not determined.

Example 3

Herbicidal Screening

Test compounds ((−) clethodim obtained in Example 1 (90–95% optical purity), (+) clethodim obtained in Example 1 (90–95% optical purity), and racemic clethodim (Select® 2EC)) were applied to three different plant species (Table III) in a spray mixture, using several different concentrations, to further evaluate the growth regulating abilities of each compound. The clethodim treatment rates ranged between 0.006 to 0.19 pounds of active ingredient per acre. Each spray mixture contained the crop oil concentrate Agridex at the concentration of 29.4 fluid ounces per acre. The total spray volume was 20 gallons per acre. Each spray mixture was prepared by adding, on an acre equivalent basis, half of the required water, the clethodim dose, and the adjuvant. The mixture was then brought to 100% by adding the remaining amount of water. In contrast to EXAMPLE 2, test plants were grown in pots in a greenhouse. Each spray mixture was sprayed onto the test plants using spray nozzles mounted within a spray chamber, calibrated to deliver the equivalent of 20 gallons per acre.

The growth stage and height of each plant species included in the assay, at the time the test compounds were applied to the test plots, are listed in Table III. Weed control observations were made 7, 15 and 21 days after application of the test compounds. All treatments were replicated three times.

These results shown in Table IV also demonstrate that (−) clethodim substantially free from (+) clethodim provides a greater degree of growth control than either the racemic form or (+) clethodim substantially free from (−) clethodim against each of the species tested. Results are expressed as a relative percentage of dead plants in a treated plot versus an untreated plot. When using (−) clethodim substantially free from (+) clethodim, the herbicidal rates may range from 0.006 to 0.022 pounds active ingredient per acre, compared with the equivalent rate range of 0.011 to 0.045 for the racemic mixture, for the same effect. Thus, with this enantiomer, the rates can be lowered and the maximum lethal dosage is reached at a lower level.

TABLE III

| Common name | Botanical name | Bayer code | Growth stage at application | Height at application (in.) |
|---|---|---|---|---|
| Giant foxtail | *Setaria faberi* | SETFA | 3–4 leaf | 2–4 |
| Crabgrass | *Digitaria sanguinalis* | DIGSA | 3–4 leaf | 2–4 |
| Annual Bluegrass | *Poa annua* | POAAN | 3 leaf | 2–4 |

TABLE IV

| | | GIANT FOXTAIL | | | CRABGRASS | | | BLUEGRASS | | |
|---|---|---|---|---|---|---|---|---|---|---|
| Day | Rate | − | + | −/+ | − | + | −/+ | − | + | −/+ |
| 7 | 0.006 | 73 | 53 | 60 | 67 | 33 | 50 | nd | nd | nd |
| | 0.011 | 90 | 73 | 80 | 77 | 43 | 67 | 20 | 7 | 13 |
| | 0.022 | 92 | 80 | 87 | 80 | 68 | 82 | 23 | 20 | 30 |
| | 0.045 | 93 | 87 | 87 | 90 | 75 | 83 | 40 | 27 | 30 |
| | 0.090 | nd | nd | nd | nd | nd | nd | 50 | 37 | 47 |
| 15 | 0.006 | 27 | 13 | 10 | 20 | 10 | 10 | nd | nd | nd |
| | 0.011 | 87 | 52 | 83 | 37 | 10 | 17 | 0 | 0 | 0 |
| | 0.022 | 90 | 78 | 88 | 70 | 20 | 67 | 10 | 0 | 10 |
| | 0.045 | 92 | 88 | 90 | 95 | 43 | 78 | 62 | 10 | 33 |
| | 0.090 | nd | nd | nd | nd | nd | nd | 77 | 40 | 73 |
| 21 | 0.006 | 7 | 0 | 0 | 0 | 0 | 0 | nd | nd | nd |
| | 0.011 | 80 | 40 | 80 | 13 | 0 | 0 | 0 | 0 | 0 |
| | 0.022 | 90 | 75 | 88 | 60 | 0 | 52 | 3 | 0 | 0 |
| | 0.045 | 95 | 90 | 90 | 94 | 30 | 73 | 75 | 0 | 30 |
| | 0.090 | nd | nd | nd | nd | nd | nd | 93 | 93 | 83 |

Data are the means of three replicates.
− clethodim is represented by "−."
+ clethodim is represented by "+."
Racemic clethodim is represented by "−/+."
nd = not determined.

Example 4

Herbicidal Screening

Test compounds ((−) clethodim obtained in Example 1 (90–95% optical purity), (+) clethodim obtained in Example 1 (90–95% optical purity), and racemic clethodim (Select®

2EC)) were applied to four different plant species, and to soil in which corn was planted immediately after treatment (Table V). Test compounds were applied in a spray mixture, using several different concentrations, to further evaluate the growth regulating abilities of each compound, and their affect on corn. The clethodim treatment rates ranged between 0.006 to 0.178 pounds of active ingredient per acre. The total spray volume was 23 gallons per acre. Three separate spray mixtures were prepared by combining (w/w %) 5 parts clethodim ((−) clethodim, (+) clethodim, or racemic clethodim), 5.5 parts Sorpol300 5×(a surfactant produced Toho Chemical Industry Co.), 8.5 parts Solvesso 100 (a hydrocarbon solvent) and the balance of xylene to form concentrates. The concentrates were diluted with water to obtain solutions of the indicated concentration of active ingredient. The test plants were grown in pots in a greenhouse. Each spray mixture was sprayed onto the test plants using a running nozzle type auto sprayer, calibrated to deliver the equivalent of 23 gallons per acre.

The growth stage and height of each plant species included in the assay, at the time the test compounds were applied to the test plots, are listed in Table V. Weed control observations were made 10, 14 and 20 days after application of the test compounds. All treatments were replicated three times.

These results shown in Table VI also demonstrate that (−) clethodim substantially free from (+) clethodim provides a greater degree of growth control than either the racemic form or (+) clethodim substantially free from (−) clethodim against each of the species tested. Results are expressed as a relative percentage of dead plants in a treated plot versus an untreated plot.

When using (−) clethodim substantially free from (+) clethodim, the herbicidal rates may range from 0.006 to 0.022 pounds active ingredient per acre, compared with the equivalent rate range of 0.011 to 0.045 for the racemic mixture, for the same effect. Thus, with this enantiomer, the rates can be lowered and the maximum lethal dosage is reached at a lower level.

TABLE V

| Plant | | | Growth stage | Height at |
|---|---|---|---|---|
| Common name | Botanical name | Bayer code | at application | application (in.) |
| Corn | *Zea mays* | ZEAMX | pre-emergent | 0 |
| Barnyard Grass | *Echinochloa crus-galli* | ECHCG | 3–4 leaf | 9–11 |
| Large Crabgrass | *Digitaria sanguinalis* | DIGSA | 3–4 leaf | 3–5 |
| Johnson Grass | *Sorghum halepense* | SORHA1 | 2–3 leaf | 7–9 |
| Giant foxtail | *Setaria faberi* | SETFA | 3–4 leaf | 8–10 |

TABLE VI

| | | PERCENT CONTROL | | | | | | | | | | | | | | |
|---|---|---|---|---|---|---|---|---|---|---|---|---|---|---|---|---|
| | | CORN | | | BARNYARD GRASS | | | LARGE CRABGRASS | | | JOHNSON GRASS | | | GIANT FOXTAIL | | |
| Day | Rate | − | + | −/+ | − | + | −/+ | − | + | −/+ | − | + | −/+ | − | + | −/+ |
| 10 | 0.006 | 0 | 0 | 0 | 0 | 0 | 0 | 0 | 0 | 0 | 0 | 0 | 0 | 0 | 0 | 0 |
| | 0.011 | 0 | 0 | 0 | 3.3 | 0 | 0 | 20 | 0 | 3.3 | 10 | 0 | 6.7 | 10 | 0 | 0 |
| | 0.022 | 0 | 0 | 0 | 37 | 13 | 18 | 40 | 23 | 37 | 40 | 20 | 40 | 47 | 20 | 43 |
| | 0.045 | 0 | 0 | 0 | 45 | 20 | 42 | 45 | 40 | 40 | 60 | 47 | 53 | 50 | 43 | 52 |
| | 0.089 | 0 | 0 | 0 | 65 | 45 | 62 | 50 | 43 | 53 | 68 | 57 | 70 | 57 | 50 | 55 |
| | 0.178 | 0 | 0 | 0 | 87 | 68 | 80 | 68 | 58 | 62 | 77 | 57 | 77 | 70 | 55 | 60 |
| 14 | 0.006 | 0 | 0 | 0 | 0 | 0 | 0 | 0 | 1.7 | 0 | 0 | 0 | 0 | 0 | 0 | 0 |
| | 0.011 | 0 | 0 | 0 | 0 | 0 | 0 | 10 | 1.7 | 1.7 | 0 | 0 | 0 | 0 | 0 | 0 |
| | 0.022 | 0 | 0 | 0 | 43 | 10 | 30 | 43 | 20 | 33 | 42 | 13 | 40 | 40 | 10 | 42 |
| | 0.045 | 0 | 0 | 0 | 50 | 40 | 45 | 50 | 40 | 43 | 67 | 50 | 63 | 55 | 45 | 52 |
| | 0.089 | 0 | 0 | 0 | 87 | 45 | 67 | 63 | 52 | 57 | 88 | 60 | 82 | 65 | 52 | 57 |
| | 0.178 | 5 | 0 | 5 | 98 | 91 | 98 | 83 | 65 | 77 | 95 | 65 | 92 | 73 | 57 | 70 |
| 20 | 0.006 | 0 | 0 | 0 | 0 | 0 | 0 | 0 | 0 | 0 | 0 | 0 | 0 | 0 | 0 | 0 |
| | 0.011 | 0 | 0 | 0 | 0 | 0 | 0 | 0 | 3 | 0 | 0 | 0 | 0 | 0 | 0 | 0 |
| | 0.022 | 0 | 0 | 0 | 50 | 0 | 18 | 30 | 13 | 20 | 20 | 0 | 33 | 35 | 0 | 32 |
| | 0.045 | 0 | 0 | 0 | 53 | 33 | 57 | 5 | 32 | 50 | 90 | 45 | 75 | 58 | 40 | 53 |
| | 0.089 | 2 | 0 | 0 | 100 | 57 | 91 | 78 | 58 | 75 | 99 | 72 | 98 | 77 | 57 | 63 |
| | 0.178 | 25 | 0 | 8 | 100 | 94 | 100 | 87 | 77 | 87 | 100 | 90 | 100 | 87 | 68 | 85 |

Data are the means of three replicates.
− clethodim is represented by "−."
+ clethodim is represented by "+."
Racemic clethodim is represented by "−/+."

While the invention has been described in detail and with reference to specific embodiments thereof, it will be apparent to one skilled in the art that various changes and modifications can be made therein without departing from the spirit and scope thereof.

What is claimed is:

1. Substantially optically pure (−)-2[(E)-1-[(E)-3-chloroallyloxyimino]propyl]-5-[2-(ethylthio)propyl]-3-hydroxycyclohex-2-enon.

2. A herbicidal composition comprising a biologically inert carrier and a herbicidally-effective amount of (−) clethodim substantially free from (+) clethodim.

3. The herbicidal composition according to claim 2, wherein the amount of (−) clethodim is greater than approximately 60% by weight of the total weight of clethodim.

4. The herbicidal composition according to claim 2, wherein the amount of (−) clethodim is greater than approximately 75% by weight of the total weight of clethodim.

5. The herbicidal composition according to claim 2, wherein the amount of (−) clethodim is greater than approximately 90% by weight of the total weight of clethodim.

6. The herbicidal composition according to claim 2, wherein the amount of (−) clethodim is about 100% by weight of the total weight of clethodim.

7. The herbicidal composition according to claim 2, further comprising one or more adjuvants.

8. The herbicidal composition according to claim 7, wherein the one or more adjuvants is a crop oil concentrate.

9. The herbicidal composition according to claim 2, further comprising one or more other biologically active chemicals.

10. A method for controlling the growth of vegetation comprising, applying to said vegetation a herbicidal composition comprising a biologically inert carrier and a herbicidally-effective amount of (−) clethodim substantially free from (+) clethodim.

11. The method of claim 10, wherein said vegetation is a grass plant.

12. The method of claim 11, wherein said grass plant is in a post-emergence growth stage.

13. The method of claim 10, wherein the herbicidally-effective amount is from about 0.010 to about 0.25 pounds active ingredient per acre.

14. The method of claim 13, wherein the herbicidally-effective amount is from about 0.022 to about 0.12 pounds active ingredient per acre.

15. The method of claim 14, wherein the herbicidally-effective amount is from about 0.045 to about 0.094 pounds active ingredient per acre.

16. The method of claim 10, wherein the amount of (−) clethodim is greater than approximately 60% by weight of the total weight of clethodim.

17. The method of claim 10, wherein the amount of (−) clethodim is greater than approximately 75% by weight of the total weight of clethodim.

18. The method of claim 10, wherein the amount of (−) clethodim is greater than approximately 90% by weight of the total weight of clethodim.

19. The method of claim 10, wherein the amount of (−) clethodim is about 100% by weight of the total weight of clethodim.

20. The method of claim 10, wherein the herbicidal composition further comprises one or more adjuvants.

21. The method of claim 20, wherein the one or more adjuvants is a crop oil concentrate.

22. The method of claim 10, wherein herbicidal composition fuirther comprises one or more other biologically active chemicals.

* * * * *